US00PP37642P2

(12) United States Plant Patent
Byrne et al.

(10) Patent No.: US PP37,642 P2
(45) Date of Patent: Aug. 25, 2026

(54) PEACH TREE NAMED 'TRH2E68L'

(50) Latin Name: *Prunus persica*
Varietal Denomination: TRH2E68L

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,148

(22) Filed: Sep. 22, 2025

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./194, 197
See application file for complete search history.

(56) References Cited

PUBLICATIONS

U.S. Appl. No. 19/336,141, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.

*Primary Examiner* — Susan Mccormick Ewoldt
(74) *Attorney, Agent, or Firm* — Dentons US LLP

(57) ABSTRACT

Disclosed is a new variety of *Prunus persica* named 'TRH2E68L'. This new variety, which requires approximately 450 chilling units of dormancy, produces an exceptionally high quality, firm semi-freestone, yellow-orange to yellow-flesh, subacid peach with a 60-90% orange-red to maroon blush over a green-yellow ground color that matures in early June in the medium chill zone and suitable for the fresh market.

5 Drawing Sheets

Latin name of the genus and species of the plant claimed: *Prunus persica.*

Variety denomination: 'TRH2E68L'.

CROSS-REFERENCE TO RELATED APPLICATIONS

Peach trees developed under the same breeding program as 'TRH2E68L' include the co-pending applications listed below.

U.S. application Ser. No. Title

U.S. Ser. No. 19/295,148 Peach Tree Named 'TRH2E122W'

U.S. Ser. No. 19/336,141 Peach Tree Named 'TX3C490LWP'

U.S. Ser. No. 19/336,385 Peach Tree Named 'TRH2B102LW'

U.S. Ser. No. 19/336,164 Peach Tree Named 'TRH3B53L'

U.S. Ser. No. 19/336,169 Peach Tree Named 'TRH3C114W'

U.S. Ser. No. 19/336,358 Peach Tree Named 'TRH2E121L'

U.S. Ser. No. 19/336,361 Peach Tree Named 'TRH3A17'

U.S. Ser. No. 19/336,363 Peach Tree Named 'TRH2E120LW'

U.S. Ser. No. 19/336,365 Peach Tree Named 'TRH3C113LW'

U.S. Ser. No. 19/336,370 Peach Tree Named 'TX2B449LW'

U.S. Ser. No. 19/336,372 Peach Tree Named 'TX2C465CW'

U.S. Ser. No. 19/336,375 Peach Tree Named 'TRH1C104LW'

U.S. Ser. No. 19/336,377 Peach Tree Named 'TRH3C111'

U.S. Ser. No. 19/336,380 Peach Tree Named 'TRH2C108W'

U.S. Ser. No. 19/336,383 Peach Tree Named 'TRH2E116L'

U.S. Ser. No. 19/336,368 Peach Tree Named 'TRH3E88LW'

BACKGROUND OF THE INVENTION

This invention relates to a peach tree and, more specifically, to peach trees referred to as a variety of *Prunus persica* named 'TRH2E68L', which requires approximately 450 chilling units of dormancy, produces a firm semi-freestone, yellow-orange to yellow-flesh, subacid peach with a 60-90% orange-red to maroon blush over a green-yellow ground color that matures in early June in the medium chill zone.

The present peach tree was the result of an ongoing Stone Fruit Breeding Program in College Station, Brazos County, Texas. To this end, controlled crosses are made each year to produce seedling populations from which improved progenies are evaluated and selected. The seedling 'TRH2E68L' was derived from a cross between a low-chill, yellow-flesh, acid-sweet, peach selection 'TXW1391-2' and a high chill subacid, yellow-fleshed nectarine selection, 'Y426-371' (not patented). 'TXW1391-2' was a low-chill, selection made from a large open pollinated population of seedlings with 'Tropic Beauty' (not patented, Sherman, W.B. and R.E. Rouse. 1989. Five new low-chill peach cultivars. Fruit Varieties Journal 43:120) as a female parent. 'Y426-371' is a high-sugar, subacid nectarine from the Stone Fruit Breeding Program in Parlier, CA. This selection has a complex parentage that includes 'O'Henry' (patented, U.S. Plant Pat. No. 2,964), 'Fairtime' (not patented), 'Southland' (not patented) and 'Sunfre' (not patented). Resulting seed from the cross between 'TXW1391-2' and 'Y426-371' were planted in 2009 in an experimental plot in Floresville, TX. 'TRH2E68L' was marked for subsequent observation in 2011 and noted as having exceptional characteristics.

'TRH2E68L' was bud grafted onto virus-free Nemaguard (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2023), Somerville (2017-2023) and Fairfield (2013-2017), Texas. This evaluation clearly demonstrated that the re-propagated trees were true to the characteristics of the original seedling in all observable aspects.

SUMMARY OF THE INVENTION

The 'TRH2E68L' peach produces firm, semi-freestone, subacid fruit that ripens in early June in the medium-chill zone and has a 60-90% orange-red to maroon blush over a green-yellow ground color. 'TRH2E68L' ripens with its female parent TXW1391-2 (not patented) and ~14 days after its pollen parent 'Y426-371' (not patented). 'TRH2E68L' differs from its low-chill yellow-flesh acid peach female parent in that it requires more chilling accumulation to fruit (~200 chill hours versus ~450 chill hours) and has subacid flesh flavor whereas it differs from its yellow-flesh, subacid nectarine pollen parent in that it requires less chilling accumulation (~450 chill hours vs. ~650 chill hours) and is a peach. Additionally, the new variety exhibits the potential to be commercialized in regions that have chilling requirements that are relatively low.

'TRH2E68L' is closely related to 'TRH3B53L' (U.S. Ser. No. 19/336,164) as they share the pollen parent 'Y426-371' and they have female parents selected from the same open pollinated seedling population of 'Tropic Beauty'. Both are subacid, yellow-flesh peaches but differ in their ripening season as 'TRH2E68L' ripens about one month later than does 'TRH3B53L'.

'TRH2E68L' differs from two other subacid peach varieties 'White Delight One' (not patented, U.S. Ser. No. 14/544,514, abandoned) and 'White Delight Two' (not patented, U.S. Ser. No. 14/544,507, abandoned) in that it has yellow rather than white flesh, showy flowers rather than non showy flowers and reniform glands rather than globose glands. 'TRH2E68L' blooms about one week earlier and requires about 100 less chilling units to fruit properly than do 'White Delight One' or 'White Delight Two'. 'TRH2E68L' ripens about the same time as 'White Delight Two' and about one month later than 'White Delight One'.

BRIEF DESCRIPTION OF THE DRAWINGS

This new variety of peach tree is illustrated by the accompanying photographs of 5-year old plants grown in Pleasanton, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
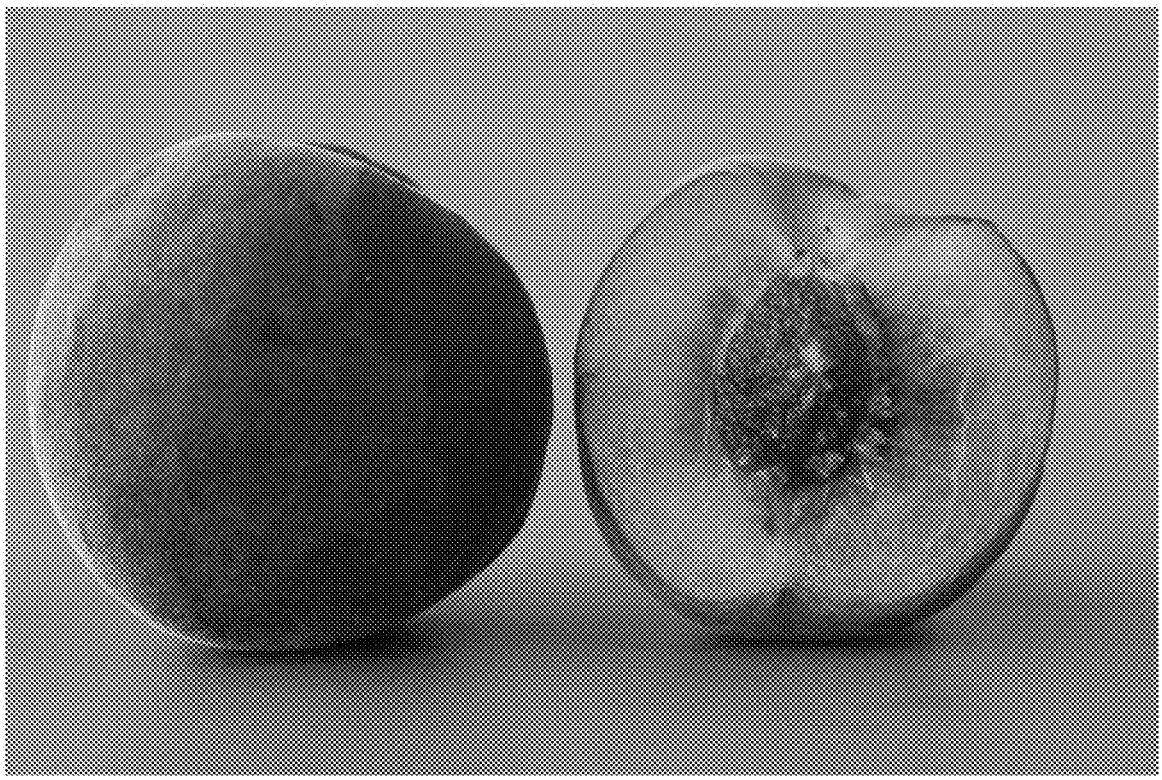
FIG. 1—Fruit of 'TRH2E68L' produced in Pleasanton, Texas showing external and internal coloration.
Figure 2:
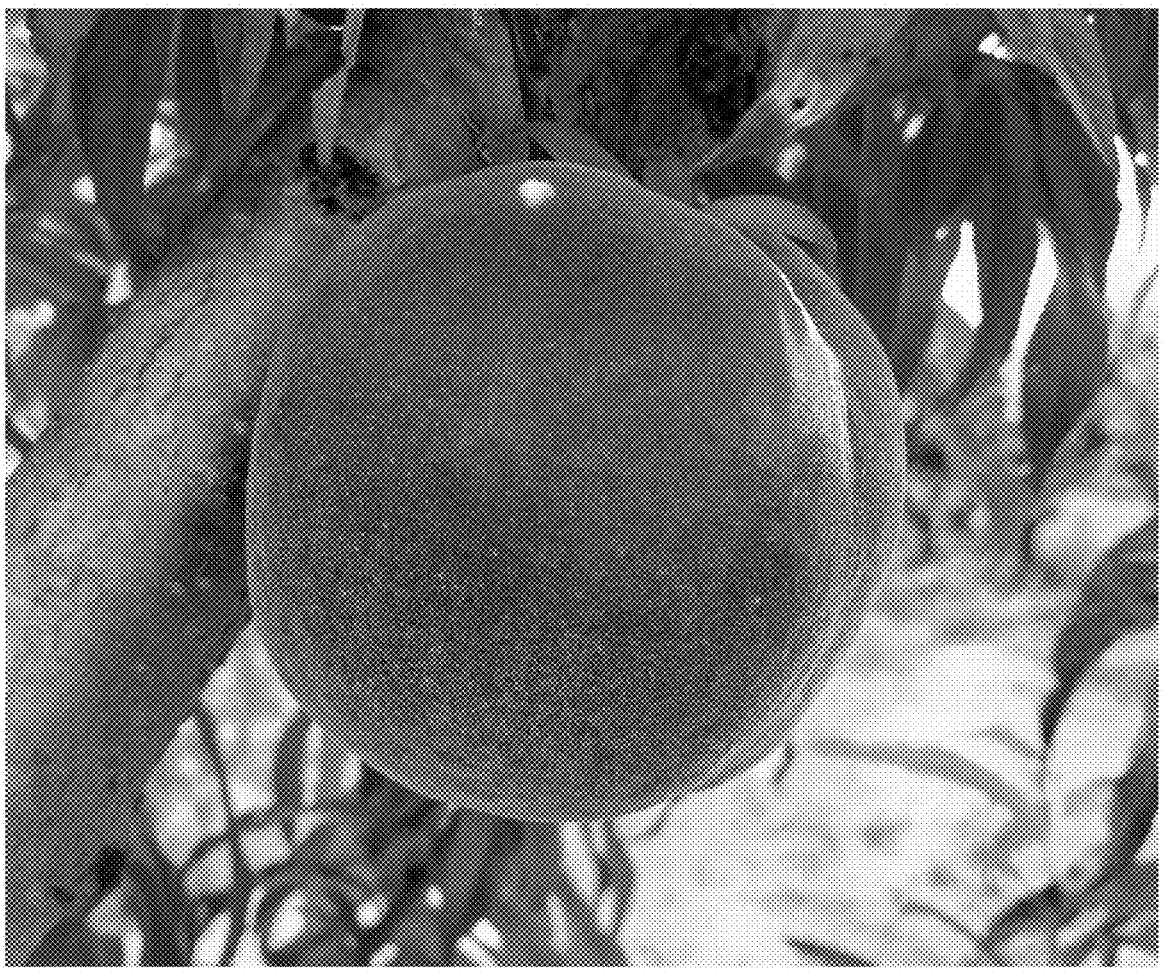
FIG. 2—'TRH2E68L' fruit produced in Pleasanton, Texas.
Figure 3:
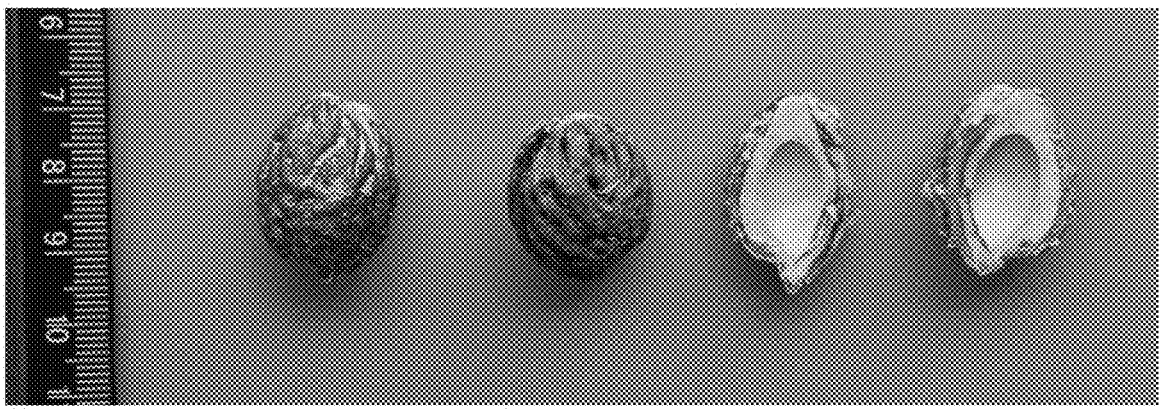
FIG. 3—Photograph of the endocarps of 'TRH2E68L' peach. Ruler is in centimeters.
Figure 4:
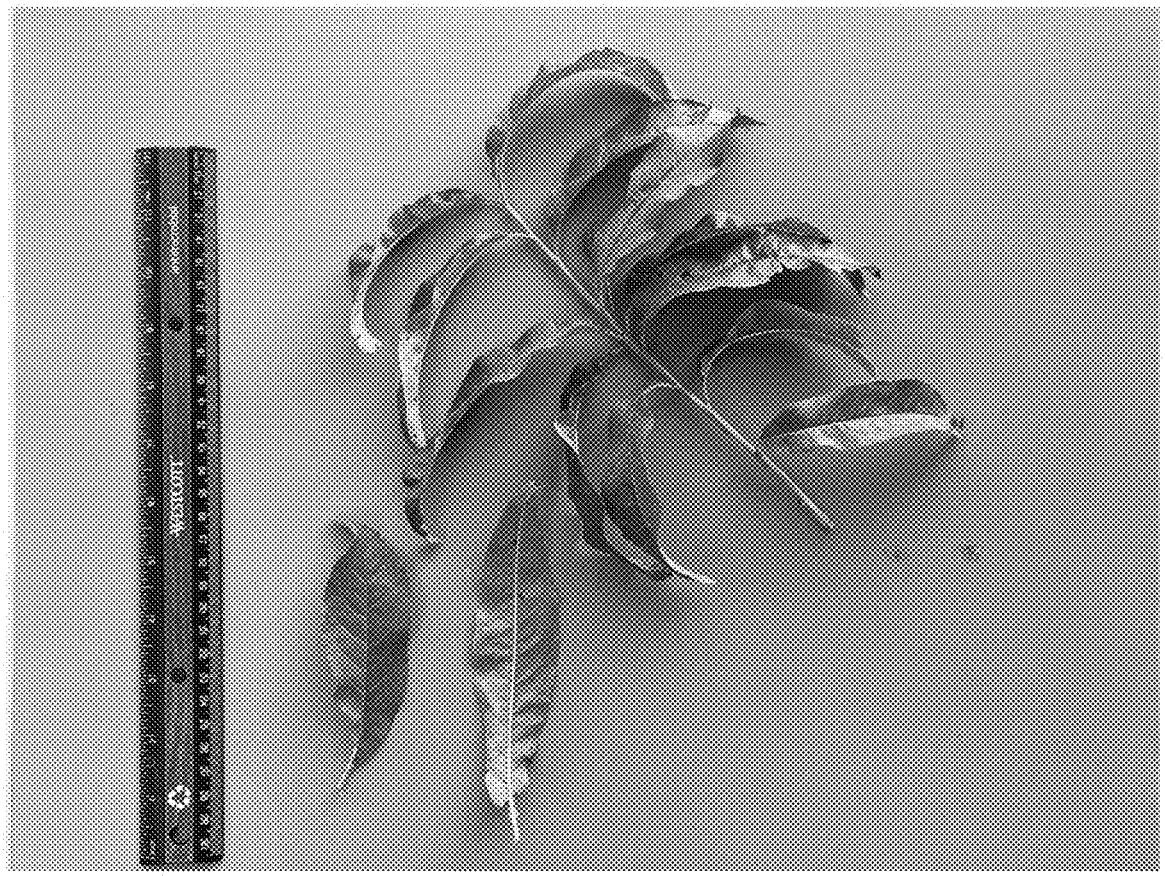
FIG. 4—A stem showing the leaves of 'TRH2E68L' peach. Ruler is in centimeters.
Figure 5:
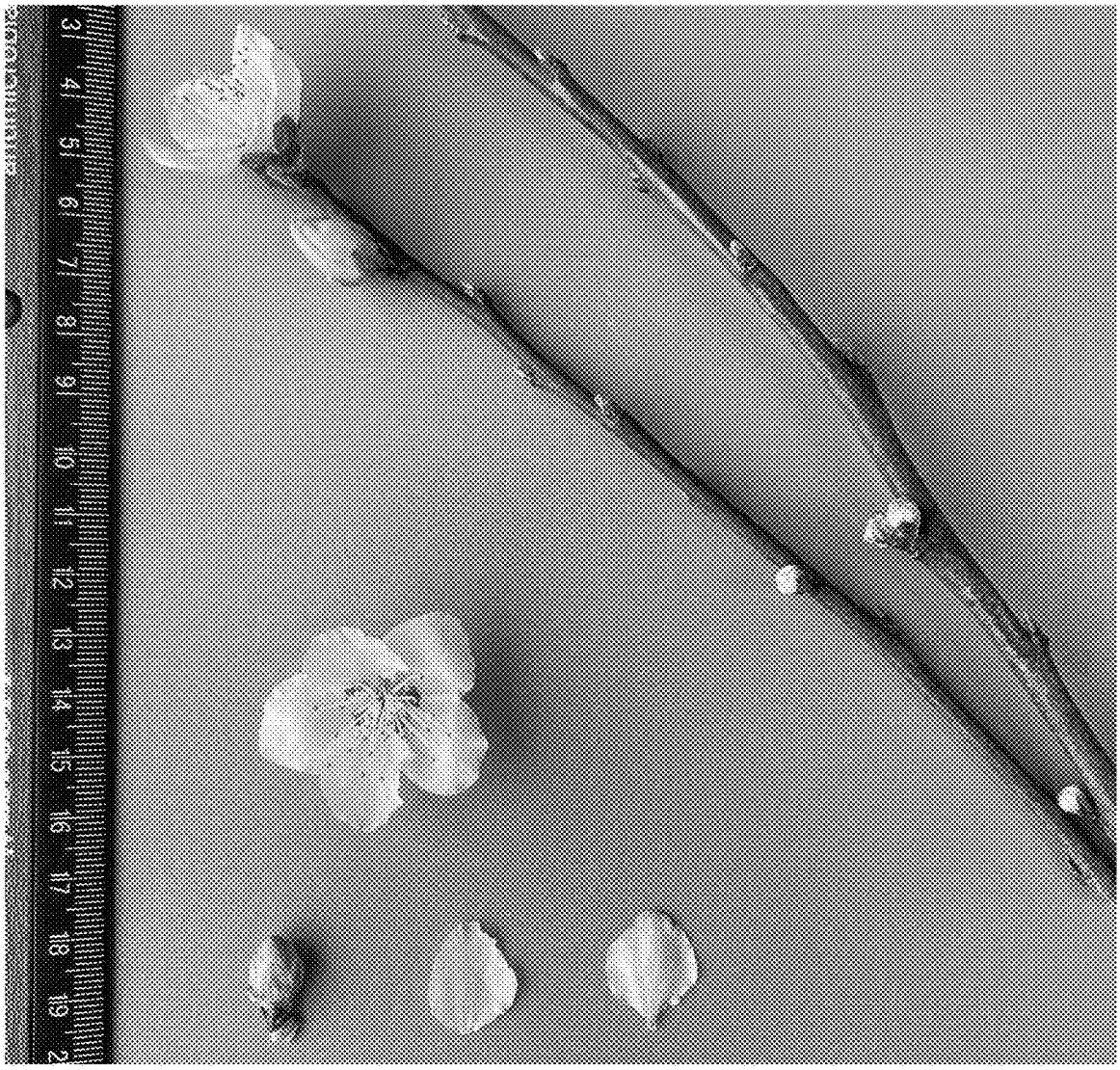
FIG. 5—A stem showing the flowers of 'TRH2E68L' peach. Ruler is in centimeters.

Referring more specifically to the pomological details of this new and distinct variety of peach tree, the following has been observed under the ecological conditions prevailing at the experimental orchards in the medium chill zone of Texas (Fairfield and College Station). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average as compared to other common peach cultivars in the medium chill zone.

*Height*.—7.5 feet (2.3 m) at the end of the 2024 growing season.

*Width*.—4 feet width (1.2 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH2E68L' peach has been trained an open center configuration but exhibits a semi spreading growth type as seen in peach varieties 'Texprince' (Byrne, D. H. and T. A. Bacon. 2004. Tex-Prince, a mid season medium chill peach. HortScience 39(3):631-632) and 'Texking' (patented, U.S. Plant Pat. No. 14,627).

*Current season growth*.—The current season growth for the new variety was approximately 1 to 3 feet (0.3-0.9 m). Medium vigor as compared to other commercial cultivars in the medium chill zone of Texas.

*Regularity of bearing*.—Regular in the absence of temperatures below 28° F. during bloom and considered hardy under typical conditions of the medium-chill zone of Texas.

Trunk:

*Size*.—Approximately 2.5 inches (6.4 cm) in diameter and 9 inches (22.9 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS 2001) present are 156A, 156B, 156C and 156D of the Greyed-White Group, 157A and 157B of the Green-White Group, 166A of the Greyed-Orange Group, 183A, 183B and 183C of the Greyed-Purple Group and N200C and N200D of the Brown Group.

Branches:

*Size*.—Considered medium for the species.

*Thickness*.—Average (about 3.8 cm in diameter as measured 10 cm from the trunk on a three-year old tree) as compared to other varieties.

*Surface texture*.—Average and appearing furrowed on wood that is several years old.

*Lenticels*.—Numerous flat, oval lenticels present. The lenticels range in size from approximately 4.0 to 6.5 mm in width and were approximately 1 to 2 mm in height.

*Current season shoots*.—Surface texture — Substantially glabrous.

*Internode length*.—Approximately 2.0 to 2.7 cm as measured in the middle of a current season stem.

*Color of mature branches*.—The predominant colors (RHS 2001) are 156A, 156B, 156C and 156D of the Greyed-White Group, 165A, 166B, 174A, 174B and 177B of the Greyed-Orange Group and 201D of the Grey Group.

Leaves:

*Size*.—Considered moderately large for the species. Leaf measurements have been taken from vigorous upright current season growth approximately at mid-shoot.

*Leaf length*.—Approximately 141 to 175 mm.

*Leaf width*.—Approximately 34 to 37 mm.

*Leaf thickness*.—Approximately less than 1 mm.

*Leaf form*.—Lanceolate.

*Leaf tip form*.—Acuminate.

*Leaf upper surface color* (*RHS* 2001).—Green varying among 137A and 137B of the Green Group.

*Leaf lower surface color* (*RHS* 2001).—Green varying among 146A and 146B of the Yellow-Green Group.

*Leaf lower mid-vein color* (*RHS* 2001).—Light yellow green, 145C of the Yellow-Green Group.

*Leaf margins*.—Form — Considered crenate. Uniformity — Considered generally uniform.

*Leaf petioles*.—Length — Approximately 5 to 10 mm. Thickness — Approximately 1 to 2 mm.

*Color* (*RHS* 2001).—Pale to medium green, 144A, 146C and 146D Group Yellow-Green Group.

*Leaf glands*.—Size — Approximately 1 mm in height and less than 1 mm in width. Number — Generally 4 per leaf.

*Type*.—Reniform. Color (RHS 2001) — Greenish brown, N199B of the Grey-Brown Group.

*Leaf stipules*.—Length — Approximately 13 to 14 mm. Form — Lanceolate.

*Color* (*RHS* 2001).—Green (N144A, N144C and 145A of the Yellow-Green Group) with reddish brown tips (172A and 172B of the Greyed-Orange Group, 178A and 178B of the Greyed-Red Group and 183A and 183B of the Greyed-Purple Group) when young. The stipules are considered early deciduous.

*Ratio of wood* (*leaf*) *buds to flowering buds*.—Generally 2 flower buds per vegetative bud.

Flowers:

*Floral buds*.—General — The floral buds are considered to be conic in form, and slightly appressed relative to the bearing shoot. Color (RHS 2001) — The mature buds are tan to light brown, (approximately 165B of the Greyed-Orange Group, 199A, 199B, N199C and N199D of the Grey-Brown Group and 200D of the Brown Group). The buds are considered hardy under typical climatic conditions in the medium chill zone of Texas. Mature Bud Length — Approximately 2 to 5 mm. Mature Bud Width — Approximately 1 to 2 mm.

*Blooming type*.—Considered early in relation to other peach cultivars commonly growing in the medium chill zone of Texas. Date of full bloom is generally in mid-February at the same time as 'Flordaking' (not patented, Andrews, C.P. 1979. 'Flordaking' peach. HortScience 14(1):81-82) and 'TexKing'.

*Flower type*.—Showy.

*Flower size*.—Flower diameter at full bloom is approximately 36 to 41 mm.

*Bloom quantity*.—Considered abundant.

*Flower bud frequency*.—Generally 2 per node.

*Petal size*.—Width — Approximately 14 to 15 mm. Length — Approximately 15 to 17 mm.

*Petal form*.—Broadly ovate.

*Petal count*.—Nearly always 5.

*Petal abaxial/adaxial color* (*RHS* 2001).—Medium pink (62B, 62C, 63D, 65B, 65C, 69A and 69B of the Red-Purple Group), becoming darker near the petal claw.

*Petal claw*.—Form — The claw is considered truncate in shape. Length — Approximately 1 to 2 mm. Width — Approximately 1 mm.

*Petal margins*.—Generally considered variable, from nearly smooth to slightly undulate.

*Petal apex*.—Generally — The petal apices appear slightly rounded.

*Flower pedicel*.—Length — Average length of 1 to 2 mm. Thickness — Approximately 1 mm. Color (RHS 2001) — A light green (144D, N144A, 144D, 145C, 145D and 150C of the Yellow-Green Group).

*Floral nectaries*.—Color (RHS 2001) — Medium orange (25A, 25B, N25A, N25B, 28A and 28B of the Orange Group and 30A, 30A, 30C, 30D, N30D and 32B of the Orange-Red Group).

*Sepals*.—Sepal number — Five sepals per flower. Surface Texture — The surface has a short, fine, wooly texture. Size — Height 5.0 mm, Width 5.6 mm. Form — Ovate. Color (RHS 2001) — Maroon with green and light grey (approximately 59A, 60A and 60B of the Red-Purple Group, 144D, N144A, 144D, 145A, 145B, 149C, 151C and 151D of the Yellow-Green Group, 156C and 156D of the Greyed-White Group and 183A, 183B, 183C, 184A, 185A, 187B and 187C of the Greyed-Purple Group).

*Floral cup* (*hypanthium*).—Surface Texture — Generally glabrous. Color — Maroon with green (approximately 59A, 59B, 60A and 60B of the Red-Purple Group, 144D, N144A, N144D, 145A, 145B, 149C, 151C and 151D of the Yellow-Green Group and 183A, 183B, 183C, 184A, 185A, 187B and 187C of the Greyed-Purple Group).

*Anthers*.—Color — Light to medium yellow (approximately 14C, 14D, 15C 15D, 16B, 16C, 16D, 17D and 18A of the Yellow-Orange Group).

*Pollen production*.—Pollen is abundant and is a medium to dark yellow color (RHS 2001, approximately 7A, 7B, 7C, 9A, 9B, 9C, 10A, 11A, 12A, 13A, 13B and 13C of the Yellow Group and 14A, 14B, 15A, 15B, 15C, 16A, 16B and 16C of the Yellow-Orange Group).

*Filaments*.—Size — Variable in length, approximately 19 to 21 mm, with the filaments being equal to the pistil. Color (RHS 2001) — White (approximately 155B, 155D and N155D of the White Group) and darkening with advanced maturity.

*Pistil*.—General — Generally equal to the general anther height. Length — Approximately 20 to 22 mm, including the ovary. Color (RHS 2001) — Considered a very light yellow-green when young (approximately 1D of the Green-Yellow Group, 150D of the Yellow-Green Group, 155A, 155B and 155C of the White Group and 157A, 157B, 157C and 157D of the Green-White Group) and becoming slightly darker with advancing senescence.

*Surface texture*.—The variety has a long, silver white pubescent pistil (RHS 2001, approximately 155A, 155B, 155C, and 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in early June. The average ripe date at College Station and Fairfield, Texas is June 8$^{th}$.

*Size*.—General — Medium large to large for the season and considered uniform. Average Cheek Diameter — Approximately 53 to 62 mm. Average Suture Diameter — Approximately 52 to 59 mm. Average Axial Diameter — Approximately 50 to 54 mm.

*Fruit form*.—Generally considered oblate. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS 2001) — Orangish-red to maroon, 34A, 34B and N34A of the Orange-Red Group and 59A and 59B of the Red-Purple Group.

*Ventral surface*.—Form — Considered uniform.

*Stem cavity*.—Width — Approximately 12 to 15 mm. Length — Approximately 20 to 25 mm. Depth — Approximately 11 to 12 mm.

*Fruit base*.—Flat and tapering.

*Fruit apex*.—Flat.

*Fruit stem*.—Length — 8 to 9 mm. Thickness — Approximately 2-3 mm. Color (RHS 2001) — Light to medium green, 144B, 144C, N144D, 145A and 145B of the Yellow-Green Group.

*Fruit skin*.—Generally considered medium or average in thickness. Surface Texture — Light in color with a medium pubescence. Skin Acidity — Considered neutral. Tenacious to Flesh — Yes at commercial maturity. Tendency to Crack — Not observed. Skin Color — Generally — Variable, with approximately 60-90% of the fruit surface covered with an orange red to maroon blush. Blush Color (RHS 2001) — Orange-red to maroon, 30A, 30B and 32B of the Orange-Red Group, 46A and 53A of the Red Group, 59A and 59B of the Red-Purple Group and N186C, 187A and 187B of the Greyed-Purple Group. Skin Ground Color (RHS 2001) — Yellow, 1A, 1B, 1C, and 1D of the Green-Yellow Group.

*Flesh color* (*RHS* 2001).—Orangish-yellow with dark pink, 13A, 13B, and 13C of the Yellow Group, 15A, 15B, 15C, 15D, 16A, 16B, 16C, 16D, 17C, 17D and 18A of the Yellow-Orange Group and 45A, 46A, 46B and 53B of the Red Group.

*Flesh fibers*.—Present, numerous and lightly colored. These fibers are present throughout the flesh.

*Stone cavity color* (*RHS* 2001).—Orangish-yellow with dark pink, 13A, 13B, 13C of the Yellow Group, 15A, 15B, 15C, 15D, 16A, 16B, 16C, 16D, 17C, 17D and 18A of the Yellow-Orange Group and 45A, 46A, 46B and 53B of the Red Group.

*Flesh texture*.—Generally, the flesh is considered firm at commercial maturity.

*Ripening*.—Generally the fruit of the present variety ripens evenly.

*Flavor*.—sweet (average Brix 13.7) with subacid flavor.

Stone:

*Attachment*.—Cling to semi freestone at commercial maturity.

*Stone size*.—Length — Approximately 24 to 29 mm. Width — Approximately 19 to 21 mm. Thickness — Approximately 15 to 16 mm.

*Fibers*.—Generally a few fibers are attached sporadically along the surface of the stone.

*Stone form*.—Variable from rounded to elliptical.

*Base angle*.—The base angle of the stone is considered wide.

*Apex shape*.—Medium.

*Stone shape*.—Ovoid.

*Stone surface*.—Surface Texture — Consists of single pits and rosettes of pits. Ridges — Numerous fine ridges are present basally and converge towards the base of the stone.

*Ventral edge*.—Considered medium.

*Dorsal edge*.—Shape — Grooved and having moderately rough edges.

*Stone color* (*RHS* 2001).—The color of the dry stone is light brown with medium to dark pink (58A, 59A, 59B, 59C, 60A, 60B, 60C, 60D, 61A, 61B and 63A of the Red-Purple Group, 165C and 165D of the Greyed-Orange Group and 183D, 184A, 184B, 184C, 185B and 185C of the Greyed-Purple Group). The color of the inside surface of the endocarp is primarily tan, 164D and 165D of the Greyed-Orange Group.

*Tendency to split*.—Splitting has not been observed.

*Kernel*.—The kernel fills the endocarp at harvest and measures approximately 3-4 mm in thickness, 9 mm in width, and 14-15 mm in length. The fresh kernels are light to medium brown (RHS 2001), 165B and 165C of the Greyed-Orange Group. When dried the shriveled kernels measure approximately 3-3.5 mm in thickness, 8-9 mm in width, and 13-14 mm in length. The colors of the shriveled kernels are medium brown, primarily 165B and N167A of the Greyed-Orange Group.

*Use*.—The subject variety, 'TRH2E68L', is a yellow-orange to yellow-flesh, subacid peach tree of early midseason maturity, which produces fruit which are firm with a 60-90% orange-red to maroon blush over a green-yellow ground color and which are useful for the fresh fruit market.

*Keeping quality*.—Average. Retains firmness and flavor after 14 days of refrigeration at 3-5° C.

*Resistance to insects and disease*.—Moderately susceptible to bacterial leaf spot [*Xanthomonas arboricola* pv. *pruni* (E. F. Smith) Dye] as is the medium chill cultivar 'TexKing'. Otherwise, no atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in College Station and Fairfield, it will be understood that variations of the usual magnitude and characteristics incident to the changes in growing conditions, fertilization, pruning, and pest control are to be expected.

What is claimed:

1. A new and distinct variety of peach tree named 'TRH2E68L', as illustrated and described herein.

* * * * *